United States Patent [19]

Corey

[11] Patent Number: 4,633,025

[45] Date of Patent: Dec. 30, 1986

[54] METHOD FOR PREPARING (+)R-2-METHYL-HEXANE-1,2-DIOL

[75] Inventor: Paul F. Corey, Elkhart, Ind.

[73] Assignee: Miles Laboratories, Inc., Elkhart, Ind.

[21] Appl. No.: 817,068

[22] Filed: Jan. 8, 1986

Related U.S. Application Data

[63] Continuation-in-part of Ser. No. 723,576, Apr. 15, 1985, abandoned.

[51] Int. Cl.$^4$ .................... C07C 29/00; C07C 31/20
[52] U.S. Cl. .................................. 568/866; 549/430; 568/844
[58] Field of Search ........................... 568/866

[56] References Cited

U.S. PATENT DOCUMENTS 2,078,534  4/1937  Groll et al. .................... 568/866
4,313,008  1/1982  Jones ............................. 568/866

OTHER PUBLICATIONS

Byers et al, "J. Chem. Soc.", (1948), pp. 1328–1331.

*Primary Examiner*—J. E. Evans
*Attorney, Agent, or Firm*—Edward P. Gray

[57] ABSTRACT

A method for preparing important stereospecific intermediates in the synthesis of prostaglandin analogs is disclosed. Said intermediates are (+)R-2-methyl-hexane-1,2-diol and (−)S-2-methyl-hexane-1,2-diol and are prepared via an asymmetric halolactonization reaction utilizing L-proline and D-proline, respectively as the chiral agent.

6 Claims, No Drawings

METHOD FOR PREPARING (+)R-2-METHYL-HEXANE-1,2-DIOL

This application is a continuation-in-part of U.S. Ser. No. 723,576 filed Apr. 15, 1985, now abandoned.

The prostaglandins as a class have been the focus of intense investigation in recent years. Being derivatives of prostanoic acid, either naturally occurring or synthetic prostaglandins possess the ability to elicit a wide range of biochemical and physiological effects including cardiovascular, nervous, reproductive, renal and gastric system responses in animals. These responses may be brought about by the administration of doses as small as about 10 ng/kg of body weight of one or more of such prostaglandins. Early isolation of these highly active compounds was achieved principally by extraction from mammalian tissues. However, such extraction processes are typically not commercially feasible nor do they provide sufficient quantities for adequate pharmacological evaluation. Synthetic methods have advanced to where sufficient quantities may be produced through complete chemical synthesis; however, this methodology suffers from the disadvantage of being essentially nonstereospecific hence leading to tedious resolution procedures which must be carried out to obtain the desired optically active isomer. It is well-known in the art that the most active prostaglandin derivatives have specific stereochemical configurations at each asymmetric carbon atom and/or double bond.

16-methyl-1,11α, 16RS-trihydroxyprost-13E-en-9-one (hereinafter referred to as TR-4698) is a prostaglandin analog which is disclosed and claimed in U.S. Pat. No. 4,132,738 issued Jan. 2, 1979 to Kluender, et al which is, as well as all other references cited herein, incorporated by reference. TR-4698 is a mixture of two isomers at the chiral C-16 position. The 16-R isomer (i.e., 16-methyl-1, 11α, 16R-trihydroxy-prost-13E-en-9-one, hereinafter referred to as TR-7133) is not believed to possess the same degree of physiological activity as the 16-S isomer (TR-7134) however, it is desirable to be able to synthesize the 16-R isomer in order to assess the degree of physiological activity, toxicology and the like which may be attributable thereto as opposed to that present in the racemic mixture or the 16-S isomer alone. This consideration may also be of value in the satisfaction of regulatory agencies involved in the approval of new drug applications for physiologically active agents. Accordingly, it has become desirable to design the synthesis of an intermediate having the requisite stereochemistry, which when ultimately incorporated into the molecule, would provide the 16-R isomer only (TR-7133) rather than the racemic mixture. The process taught herein is directed to the synthesis of (+)R-2-methyl-hexane-1,2-diol (an intermediate for the preparation of the 16-R isomer, TR-7133). Said intermediate is prepared via an asymmetric halolactonization reaction utilizing L-proline as the chiral agent which may then be subsequently incorporated into the synthesis of TR-7133 as described hereinafter.

DESCRIPTION OF PERTINENT ART

Various techniques have been utilized in the preparation or isolation of physiologically active prostaglandin isomers. One such technique is to utilize a resolved intermediate possessing the appropriate stereochemistry at the chiral center for incorporation into the molecule. For example, Pappo, et al in "Chemistry, Biochemistry and Pharmacological Activity of Prostanoids", edited by S. M. Roberts and F. Scheinmann, Pages 17–26, Pergammon Press, N.Y., 1978, teach the resolution of racemic 2-hydroxy-2-methyl-hexanoic acid via its naphthylethylamine salt for preparation of a chiral acetylenic alcohol. (This optically active acetylenic alcohol may then be incorporated as the "right-hand" portion of the prostaglandin analog by following known techniques). However, the classical resolution of the racemic 2-hydroxy-2-methyl-hexanoic acid is tedious at best and requires an expensive, optically active amine.

Another approach taught by Y. Fujimoto, J. Yadev, and C. Sih in *Tetrahedron Letters*, 21, 1481 (1980) prepares (−)S-2-methyl-hexane-1,2-diol from (+)citramalic acid, the chiral diol then being used to prepare the corresponding optically active acetylenic alcohol. The disadvantage of this method is that the citramalic acid must be prepared from mesaconic acid using an isolated microbial enzyme.

S-s. Jew, S. Terashima and K. Koga in *Tetrahedron*, 35, 2337, et seq (1970), and papers cited therein, teach the use of an asymmetric halolactonization reaction to prepare optically active αα-disubstituted-α-hydroxy acids from α, β-unsaturated acids. However, the technique described therein suffers from the disadvantage of being unable to render the S-isomer of the resulting α,α-disubstituted-α-hydroxy acid in high optical purity. For example, Jew, et al teach that when trans-2-methyl-2-butenoic acid is utilized as the starting compound, the R-isomer of the resulting 2-hydroxy-2-methyl butanoic acid is formed in high predominance to the S-isomer (approximately 95:5, respectively). Similarly, when cis-2-methyl-2-butenoic acid was investigated as the starting material, the R-isomer of the resulting 2-hydroxy-2-methyl butanoic acid was still predominant although a shift toward the S-isomer was observed (approximately 60:40, respectively).

The invention described herein teaches the preparation of (+)R-2-methyl-hexane 1,2-diol from methacryloyl chloride. As described previously, this intermediate can be used to prepare the optically active 16-R isomer of prostaglandin analogs such as TR-7133.

SUMMARY OF THE INVENTION

The present invention is directed to a method for preparing the stereospecific prostaglandin intermediate (+)R-2-methyl-hexane-1,2-diol. Said method includes the steps of reacting methacryloyl chloride with L-proline in the presence of a base forming an amide of the formula:

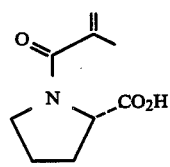

This amide is then reacted with N-bromosuccinimide in an aprotic polar solvent forming a bromolactone of the formula:

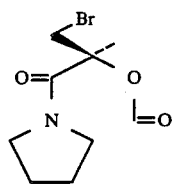

Said bromolactone is then hydrolyzed with aqueous hydrobromic acid forming a bromo-acid of the formula:

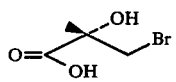

This bromo-acid is then reduced with a mixture of bo-rane-tetrahydrofuran forming a bromodiol of the formula:

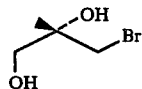

Said bromodiol is then treated with dimethoxypropane and toluene sulfonic acid forming an acetonide of the formula:

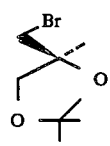

This acetonide is then reacted with dipropyl cuprate forming an alkylation product of the formula:

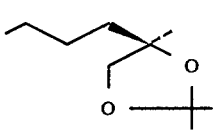

Said alkylation product is then reacted with acidic, aqueous tetrahydrofuran to effect formation of (+)R-2-methyl-hexane-1,2-diol.

DETAILED DESCRIPTION OF THE INVENTION

The method of the present invention provides for the preparation of (+)R-2-methyl-hexane-1,2-diol via an asymmetric halolactonization reaction utilizing L-proline as the chiral agent. The reaction scheme for the preparation of said diol is depicted in Table 1.

TABLE 1

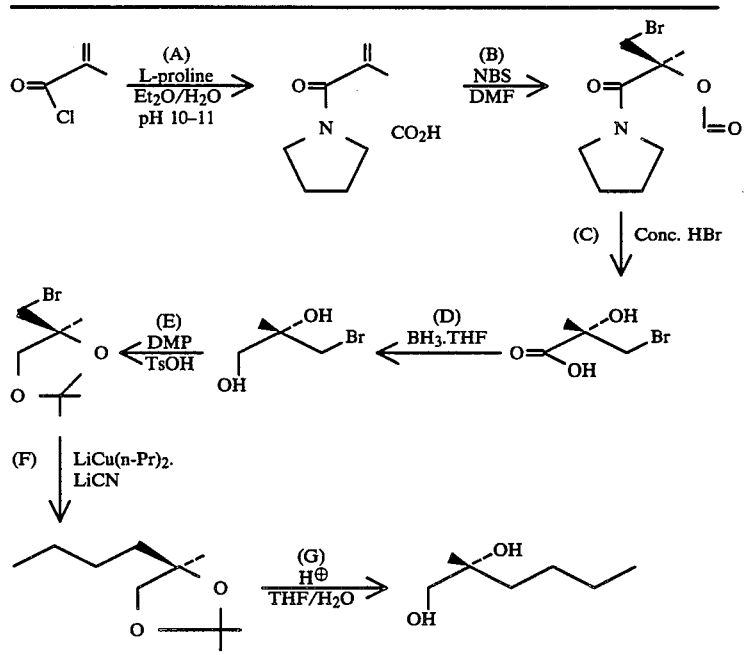

N-methacryloyl-L-proline is first prepared by the dropwise addition of methacryloyl chloride to an aqueous mixture of L-proline, sodium bicarbonate and diethyl ether (pH maintained at about 10–11 throughout) and the mixture is stirred at ambient temperature for about 15 minutes to about 2 hours (step A). The N-methacryloyl-L-proline is then isolated utilizing conventional extraction techniques. Bromolactonization is then achieved by the addition of N-bromosuccinimide (NBS) to the L-proline derivative in an aprotic solvent such as dimethyl- formamide (DMF) followed by stirring at ambient temperature for about 12 to about 36 hours (step B).

The resulting bromolactone is isolated and then heated (about 100° to 110° C.) with aqueous concentrated hydrobromic acid for about 15 to about 24 hours (step C). The resulting bromo-acid is isolated by conventional techniques and is then reduced by treatment with a mixture of $BH_3$ in tetrahydrofuran (step D). This mixture is stirred at ambient temperature for about 12 to about 24 hours after which the reaction is quenched by the addition of small amounts of a mixture of tetrahydrofuran/water (about 1:1). The resulting bromodiol is then recovered using conventional techniques as described hereinafter. The bromodiol is then protected as its acetonide (step E) by reacting said bromodiol with dimethoxypropane (DMP) and a catalytic amount of toluenesulfonic acid at ambient temperature with stirring for about 8 to about 24 hours thereby forming said acetonide.

A solution of n-propyl lithium in anhydrous diethyl ether is prepared (maintained under an inert gas atmosphere at around −40° C.) and then treated with CuCN. See B. H. Lipshutz, et al, *J. Am. Chem. Soc.*, 103, 7672 (1981). The resulting cuprate solution is then added to a solution of the above-acetonide in diethyl ether (step F) and this mixture is then maintained in an inert gas atmosphere at about 0° C. with stirring for about 15 minutes to about 2 hours. This stirred mixture is then poured into a solution of saturated aqueous ammonium chloride (pH about 8-9) and shaken. The resulting alkylation product is recovered by conventional means and is then treated with acidic aqueous tetrahydrotetrahydrofuran (step G) to form the desired (+)R-2-methyl-hexane-1,2-diol.

The (+)R-2-methyl-hexane-1,2-diol prepared by the method of this invention may then be utilized (by following known techniques) in the formation of certain stereospecific prostaglandin analogs, described briefly as follows. Utilizing the procedure of Pappo, et al, cited supra, the (+)R-2-methyl-hexane-1,2-diol can be used to prepare the corresponding stereospecific acetylenic alcohol, i.e., 4-methyloct-1-yn-4R-ol. See the reaction sequence shown in Table 2.

TABLE 2

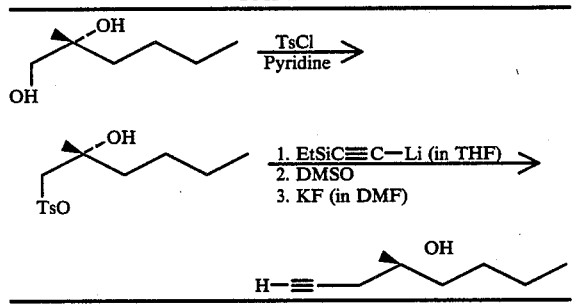

As depicted in Table 2, (+)R-2-methyl-hexane-1,2-diol is treated with tosyl chloride in pyridine to form the monotosylate. A three equivalent excess of lithium triethylsilylacetylide (formed in situ) is added to the monotosylate forming an intermediate epoxide which is opened upon treatment with dimethyl sulfoxide (DMSO). Purification after work-up with potassium fluoride (KF) in dimethylformamide renders the desired stereospecific acetylenic alcohol, 4-methyloct-1-yn-4R-ol.

As taught by Kluender et al, (U.S. Pat. No. 4,132,738, cited supra) the above acetylenic alcohol is then converted to the corresponding iodovinyl alcohol. The hydroxyl function of the iodovinyl alcohol is protected with an acid-labile hydroxy protecting group (or alternatively, the hydroxyl group of the acetylenic alcohol can be protected prior to conversion of the alcohol to the iodovinyl compound). The hydroxy-protected iodovinyl alcohol is then lithiated with t-butyllithium and reacted with a solubilized ligand complex of a copper (I) compound such as (hexamethylphosphoroustriamide)$_2$-copper (I) pentyne to yield the corresponding organolithio-cuprate. This organolithiocuprate is then reacted with 4R-(tetrahydropyran-2-yloxy)-2-[7-tetrahydro- pyran2-yloxy)heptyl]-2-cyclopent-2-enone to form the tetrahydropyran-protected form of TR-7133. Said protected form is then hydrolyzed with a weak acid to render TR-7133. Clearly, one skilled in the art will appreciate that other prostaglandin analogs may be prepared using the optically active (+)-R-2-methylhexane-1,2-diol by the procedure described above or other techniques known to the art.

The following examples are set forth as a means of illustrating the present invention and are not to be construed as a limitation thereon.

EXAMPLE 1

Preparation of (+)R-2-methyl-hexane-1,2-diol (a) N-methacryloyl-L-proline.

A mechanically stirred mixture of L-proline (42.0 grams, g), NaHCO$_3$(148 g), H$_2$O (680 milliliters, ml) and diethyl ether (280 ml) was maintained in an ambient temperature bath at pH 10.5–10.7 (adjusted by the addition of concentrated aqueous NaOH), then treated portionwise over 20 minutes with a solution of redistilled methacryloyl chloride (40 ml) in diethyl ether (20 ml). Additional concentrated aqueous NaOH was added as needed to keep the pH at 10.5–10.7. Upon addition of all of the methacryloyl chloride (and pH stabilization), the mixture was stirred for 20 minutes at ambient temperature. The resulting immiscible phases were separated and the aqueous phase was extracted with two 250 ml portions of diethyl ether. The combined organic extracts were washed with H$_2$O (50 ml), and the aqueous extract was added to the aqueous phase which phase was then acidified to pH 1 with concentrated aqueous HCl and then extracted with four 250 ml portions of ethyl acetate. The combined ethyl acetate extracts were washed with about 100 ml of brine (saturated aqueous sodium chloride solution) and then dried over Na$_2$SO$_4$. The resulting solution was filtered and concentrated in vacuo to about 230 ml and then heated to boiling, diluted with hexane (80 ml) and allowed to cool. Upon cooling, the desired N-methacryloyl-L-proline spontaneously crystallized as chunky white prisms (51.3 g). The concentrated mother liquor yielded a second crop of crystals (4.26 g) when crystallized as described above. A portion of the first crop was recrystallized twice from ethyl acetate to give an analytical sample, m.p. 102°–104.5° C., having the following spectral characteristics:

ir (CHCL$_3$) 2970, 1712, 1610, 1455, 1440, 1200, 915 cm$^{-1}$; nmr (CDCl$_3$)δ11.7 (s, 1H), 5.05–5.40 (m, 2H), 4.60 (t, J=6, 1H), 3.64 (t, J=6, 2H), 1.90–2.50 (m, 4H), 1.96 (s, 3H); C$^{13}$ nmr (CDCl$_3$) ppm 174.7, 171.9,140.5, 117.5, 59.1, 49.5, 28.9, 25.0, 19.6; [α]$_D$=-136.41 (C=1.111 in CHCl$_3$), the optical rotation varying with concentration.

Anal. Calcd. for C$_9$H$_{13}$NO$_3$: C, 59.00; H, 7.15; N, 7.65. Found: C, 58.90; H, 6.99; N, 7.67.

(b) 3S-Bromomethyl-3-methyl-1,4-dioxo-3,4,6,7,8, 8αS-hexahydro-1H-pyrrolo [2,1-c][1,4]oxazine 36.6 g of the title compound of Example 1(a) was added to 500 ml of dry (4Å) dimethylformamide and was maintained at ambient temperature under an inert gas atmosphere (protected from light) and was treated with recrystallized N-bromosuccinimide (71.2 g). The resulting mixture was stirred for about 20 hours and was then poured into a mixture of saturated aqueous sodium bicarbonate (2 liters) and ethyl acetate (800 ml) and shaken vigorously. The resulting immiscible phases were separated and the aqueous phase was extracted three times with 500 ml portions of ethyl acetate. The combined ethyl acetate extracts were washed eight times with 125 ml portions of saturated aqueous $Na_2S_2O_3$. The $Na_2S_2O_3$ extracts were combined and washed with one 100 ml portion of ethyl acetate, and the ethyl acetate extracts were combined and washed three times with 330 ml portions of $H_2O$. The aqueous extracts were combined and washed with 200 ml of ethyl acetate. The ethyl acetate extracts were again combined and washed with 300 ml of brine, dried over $Na_2SO_4$, filtered and concentrated in vacuo to about 250 ml. This concentrate was then heated (to dissolve any solids) and diluted with 50 ml of isopropyl ether and allowed to cool. The title compound (of Example 1b) spontaneously crystallized as fine white needles (29.6 g). Concentration of the mother liquor yielded an additional 3.9 g of product. A portion of the first crop was recrystallized from ethyl acetate to afford an analytical sample, m.p. 157°–158° C., having the following spectral characteristics:

ir ($CHCl_3$) 2980, 1757, 1670, 1358, 1070 $cm^{-1}$; nmr ($CDCl_3$)$\delta$4.56 (m, 1H), 3.97 (d, $|J_{AB}|=11.2$, 1H) and 3.53 (d, $|J_{AB}|=11.2$, 1H) [center of pattern: 3.75, $\Delta\nu_{AB}=19.7Hz$], 3.50–3.90 (m, 2H), 2.30–2.70 (m, 1H), 1.80–2.30 (m, 3H), 1.73 (s, 3H); $C^{13}$ nmr ($CDCl_3$) ppm 166.4, 164.3, 85.4, 58.3, 45.5, 37.9, 29.9, 24.7, 21.8; $[\alpha]_D = -131.4$ (C=1.9745 in $CHCl_3$).

Anal. Calcd. for $C_9H_{12}BrNO_3$:C, 41.24; H, 4.62; N, 5.34. Found: C, 41.58; H, 4.78; N, 5.20.

(c) (−)S-2-Hydroxy-2-methyl-3-bromo-propionic acid

A solution of 13.0 g of the title compound of Example 1(b) in 160 ml of 48% aqueous HBr was heated in a 100°–105° C. bath for 16 hours and then cooled. The solution was then poured into 800 ml of brine and extracted twice with 500 ml portions of $CH_2Cl_2$. The combined organic extracts were washed with 300 ml of $H_2O$, and the aqueous layer was then extracted with three 500 ml portions of ethyl acetate. The ethyl acetate extracts were combined and washed with three 100 ml portions of brine, and the resulting solution was dried over $Na_2SO_4$, filtered and evaporated in vacuo. Crystallization from 125 ml of hot ethyl acetate/hexane (1:4) yielded 6.7 g of the title compound (of Example 1c) as colorless rods and needles. The mother liquor was concentrated and crystallized from a minimum of hot $CHCl_3$ to yield an additional 1.4 g of the title compound, m.p. 111.5°–114.0° C. The material had the following spectral characteristics:

ir ($CHCl_3$) 3500 (br), 2970 (br), 1722 (br), 1450, 1182, 1080 $cm^{-1}$; nmr ($CDCl_3$)$\delta$6.80 (v.br.s, 2H), 3.87 (d, $|J_{AB}|=10.4$, 1H) and 3.39 (d, $|J_{AB}|=10.4$, 1H) [center of pattern: 3.63, $\Delta\nu_{AB}=21.7$ Hz], 1.62 (s, 3H); $C^{13}$ nmr ($CDCl_3$) ppm 177.9, 74.3, 39.6, 24.2; $[\alpha]_{365}=-31.2$ (C=1.4 in $CHCl_3$); $[\alpha]_D = -10.9$ (C =1.4 in $CHCl_3$).

Anal. Calcd. for $C_4H_7BrO_3$: C, 26.25; H, 3.86. Found: C, 26.03; H, 3.89.

(d) (+)S-2-Methyl-3-bromo-propane-1,2-diol

A solution of 3.78 g of the title compound of Example 1(c) in 20 ml of anhydrous THF was maintained under an inert gas atmosphere and cooled in an ice bath. To this solution was added a 1M $BH_3$·THF solution (65 ml). The resulting reaction mixture was allowed to warm to ambient temperature and was stirred for about 20 hours. The reaction was quenched by the addition of small portions of a mixture of $THF/H_2O$ (1:1) until $H_2$ evolution ceased, followed by the addition of water. This mixture was then heated briefly, then cooled and extracted three times with 25 ml portions of brine. The combined brine layers were extracted with 50 ml of diethyl ether. The organic extracts were then combined and dried over $Na_2SO_4$, filtered and evaporated in vacuo. Short path vacuum distillation afforded about 3.3 g of the title compound (of Example 1d) as a colorless viscous syrup, boiling point (b.p.) 63°–64° C. (0.14 torr) having the following spectral characteristics:

ir ($CHCl_3$) 3400 (br), 2930, 1460, 1380, 1042, 890 $cm^{-1}$; nmr ($CDCl_3$)$\delta$3.61 (d, $|J_{AB}|=6.1$, 1H) and 3.53 (d, $|J_{AB}|=6.1$, 1H) [center of pattern: 3.60, $\Delta\nu_{AB}=6.7$ Hz], 3.50 (s, 2H), 2.75 (br.s, 2H) (OH, very variable), 1.31 (S, 3H); $C^{13}$ nmr ($CDCl_3$) ppm 72.0, 67.5, 40.4, 22.6; $[\alpha]_{365}= +10.72$ (C=1.501 in $CHCl_3$).

Anal. Calcd. for $C_4H_9BrO_2$; C, 28.42; H, 5.37. Found: C, 28.42; H, 5.18.

(e) (-)S-1,1-Dimethyl-4-bromomethyl-4-methyl-2, 3-dioxolane

A solution of 3.38 g of the title compound of Example 1(d) in acetone (50 ml) and freshly distilled dimethoxypropane (3.0 ml) was maintained at ambient temperature under an inert gas atmosphere. To this was added a catalytic amount of toluene sulfonic acid monohydrate and the resulting reaction mixture was stirred for about 15.5 hours after which it was filtered through a plug of alumina and evaporated in vacuo. Short path distillation at atmospheric pressure gave 3.57 g of the title compound (of Example 1e) as a colorless, pungent liquid (b.p. 176°–179° C., 760 torr), very unstable to traces of acid. The material had the following spectral characteristics:

ir (thin film) 2975, 2860, 1372, 1210, 1100, 1055 $cm^{-1}$; nmr ($DMSO-d^6$)$\delta$4.07 (d, $|J_{AB}|=8.8$, 1H) and 3.62 (d, $|J_{AB}|=8.8$, 1H) [center of pattern: 3.84, $\Delta\nu_{AB}=20.1$ Hz], 3.49 (M, 2H), 1.36 (s, 3H), 1.34 (s, 3H), 1.31 (s, 3H); $C^{13}$ nmr ($DMSO-d^6$) ppm 109.6, 79.7, 71.9, 39.7, 27.1, 26.6, 23.2; $[\alpha]_{365}=-55.04$ (C=1.9075 in acetone); $R_f=0.546$ (7.5% $Et_2O$ in $CH_2Cl_2$).

(f)
(+)R-1,1-Dimethyl-4-(n-butyl)-4-methyl-1,3-dioxolane

A solution of 1.26 M n-propyl lithium (49.7 ml; prepared from lithium wire and dry n-propyl bromide in diethyl ether) was maintained under an inert gas atmosphere and cooled in a −40° C. bath and treated with 2.85 g of CuCN (dried over $P_2O_5$ in vacuo). The resulting beige-colored nearly homogeneous cuprate solution was stirred for about 5 minutes at −40° C. then transferred to an ice bath and stirred for an additional 15 minutes. This solution was then quickly pressed into a rapidly stirred solution of the title compound of Example 1e (2.18 g) in 10 ml of diethyl ether (similarly maintained under an inert gas atmosphere at about 0° C.). The resulting mixture was stirred at 0° C. for about 50 minutes and then blended into a solution of saturated aqueous $NH_4Cl$ made basic (pH 8.5–9.0) with concentrated aqueous $NH_4OH$. The resulting immiscible phases were separated and the aqueous phase was extracted with three 125 ml portions of diethyl ether. The diethyl ether extracts were combined and washed twice with 20 ml portions of brine, dried over $MgSO_4$, filtered and evaporated in vacuo to give about 1.2 g of the title compound (of Example 1f) as a pale yellow oil. This material was chromatographed on a ⅜"×19" silica 5 gel column eluted with 1.75% diethyl ether in $CH_2Cl_2$ and the major band ($R_f$=0.34) was isolated. A quick short path distillation afforded an analytical sample, b.p. 130° C. (approx.) at 760 torr. The material had the following spectral characteristics:

ir (thin film) 2930, 2860, 1455, 1370, 1205, 1055 cm$^{-1}$; nmr (CDCl$_3$)δ3.79 (d, $|J_{AB}|$=8.2, 1H) and 3.63 (d, $|J_{AB}|$=8.2, 1H) [center of pattern: 3.71, $\Delta\nu_{AB}$=7.5 Hz, 1.15-1.70 (m, 6H), 1.39 (s, 3H), 1.38 (s, 3H), 1.26 (s, 3H), 0.90 (t, J =6, 3H); C$^{13}$ nmr (CDCl$_3$) ppm 109.1, 81.4, 74.3, 40.1, 27.4, 27.2, 26.8, 24.9, 23.3, 14.0; $[\alpha]_{365}$=+6.27 (C=1.2065 in acetone).

(g) (+)R-2-Methyl-hexane-1,2-diol 300 mg of the title compound of Example 1(f) was treated with a solution of 2N HCl/Tetrahydrofuran (1:1) at ambient temperature for about 2.5 hours. The mixture was diluted with 20 ml of diethyl ether and shaken vigorously. The immiscible phases were separated and the aqueous phase was extracted with three 15 ml portions of diethyl ether. The ether extracts were then combined and extracted once with saturated aqueous sodium bicarbonate (10 ml) and brine (10 ml), dried over sodium sulfate, filtered and evaporated in vacuo to give the crude product (178 mg). Kügelrohr distillation (<0.1 torr) afforded the desired (+)R-2-methyl-hexane-1,2-diol as a colorless, viscous oil that distilled over at between 40°-90° C. (pot temperature). The product was identical to that prepared by the lithium aluminum hydride reduction of (−)R-2-hydroxy-2-methyl-hexanoic acid which acid was resolved from racemic 2-hydroxy-2-methyl-hexanoic acid as described by Pappo et al, supra. The (+)R-2-methyl-hexane-1,2-diol prepared as described in this example had the following spectral characteristics:

ir (CHCl$_3$) 3380 (br), 2940, 2920, 1460, 1375, 1030, 890 cm$^{-1}$; nmr (CDCl$_3$)δ3.43 (br.s, 2H), 2.57 (br.s, 2H) (OH), 1.20-1.60 (m, 6H), 1.16 (s, 3H), 0.92 (t, J =6, 3H); C$^{13}$ nmr (CDCl$_3$) ppm 73.1, 69.8, 38.6, 26.0, 23.3, 14.0 (one coincidental band); $[\alpha]_D$=+4.03 (C=2.5795 in CHCl$_3$); $[\alpha]_{365}$=+12.54 (C =2.5795 in CHCl$_3$).

By utilizing substantially analagous procedures, the stereoisomer, (−)S-2-methyl-hexane-1,2-diol is prepared as described in the following example.

EXAMPLE 2

Preparation of (−)S-2-methyl-hexane-1,2-diol

(a) N-methacryloyl-D-proline

D-Proline (50 g) was dissolved in 430 ml of 20% aqueous sodium hydroxide and the resultant solution was stirred with ice bath cooling as 217 ml ether was added followed by dropwise addition of 50 g of methacryloyl chloride in 400 ml ether over about 45 minutes. After another 30 minutes, the aqueous phase was removed and washed once with additional ether. The aqueous phase was then acidified with concentrated hydrochloric acid and extracted three times with ethyl acetate. These combined ethyl acetate extracts were evaporated in vacuo. The resultant residue was crystallized from a mixture of toluene and petroleum ether to yield the title compound, N-methacryloyl-D-proline, which was then recrystallized from acetone/petroleum ether to yield 51.5 g (53%) of purified material.

(b) 3R-Bromomethyl-3-methyl-1,4-dioxo-3,4,6,7,8,8αR-hexahydro-1H-pyrrolo[2,1-c][1,4]oxazine 51.5 g of the title compound of Example 2(a) was added to 722 ml of dry dimethylformamide and was maintained at ambient temperature under argon as 100g of recrystallized N-bromosuccinimide was added. The resultant mixture was stirred for 18 hours and then poured into 1900 ml of saturated aqueous sodium bicarbonate solution. The resultant mixture was extracted three times with ethyl acetate. The combined extracts were washed with water twice, dried over sodium sulfate and evaporated in vacuo to remove solvent. The residue was dissolved in 170 ml hot ethyl acetate and 120 ml of isopropanol. Petroleum ether was added to the hot solution which was then cooled to crystallize the product which was removed by filtration and dried. The yield was 21.5 g of purified title compound of Example 2(b): m.p. 156°-158° and having ir and nmr spectral characteristics identical to its enantiomer of Example 1(b).

(c) (+)R-2-Hydroxy-2-methyl-3-bromopropionic Acid

A mixture of 5 g of the title compound of Example 2(b) and 50 ml of 48% aqueous hydrobromic acid was heated at 105° C. bath temperature for 16 hours and then cooled. The resultant mixture was poured into 50 ml of saturated brine and extracted four times with 100 ml portions of ethyl acetate. The combined extract was dried over magnesium sulfate and then evaporated in vacuo to remove solvent. The residue was crystallized from ethylacetate/hexane to yield 2.7 g of purified title compound of Example 2(c) as white needles: m.p. 108°-111° ,$[\alpha]_D$+10.1° (cl.48,CHCl$_3$), $[\alpha]_{365}$ +28.7° (cl.48, CHCl$_3$), nmr and ir are identical to the enantiomer of 1c).

(d) (−)S-2-methyl-hexane-1,2-diol

Following the procedures set forth in Example 1 (d) through 1(g), the compound (−)S-2-methyl-hexane-1,2-diol is prepared and may be incorporated into the synthesis of TR-7134 as described, supra.

While the present invention has described in detail a method for preparing (+)R-2-methyl-hexane-1,2-diol and (−)S-2-methyl-hexane-1,2-diol, it is to be recognized that analagous procedures can be used to prepare like-substituted alkane-diols. Accordingly, such procedures are deemed to be contemplated equivalents to the claimed method of the present invention.

What is claimed is:

1. A method for preparing (+)R-2-methyl-hexane-1,2-diol comprising:
   (a) reacting methacryloyl chloride with L-proline in the presence of a base forming an amide of the formula:

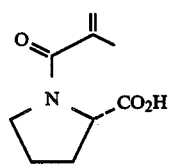

(b) reacting said amide with N-bromo-succinimide in an aprotic polar solvent forming a bromolactone of the formula:

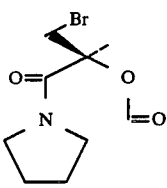

(c) hydrolyzing said bromolactone with aqueous hydrobromic acid forming a bromo-acid of the formula:

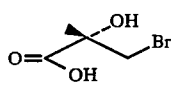

(d) reducing said bromo-acid with a mixture of borane-tetrahydrofuran forming a bromodiol of the formula:

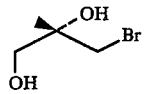

(e) treating said bromodiol with dimethoxy-propane and toluenesulfonic acid forming an acetonide of the formula:

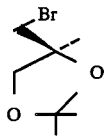

(f) reacting said acetonide with dipropyl cuprate forming an alkylation product of the formula:

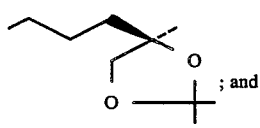

(g) reacting said alkylation product with acidic, aqueous tetrahydrofuran to effect formation of (+)R-2-methyl-hexane-1,2-diol.

2. The method of claim 1 wherein the base according to step (a) thereof is sodium hydroxide.

3. The method of claim 1 wherein the aprotic polar solvent according to step (b) thereof is dimethylformamide.

4. A method for preparing (−)S-2-methyl-hexane-1,2-diol comprising:

(a) reacting methacryloyl chrloride with D-proline in the presence of a base forming an amide of the formula:

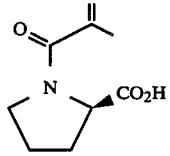

(b) reacting said amide with N-bromo-succinimide in an aprotic polar solvent forming a bromolactone of the formula:

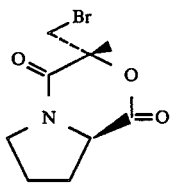

(c) hydrolyzing said bromolactone with aqueous hydrobromic acid forming a bromo-acid of the formula:

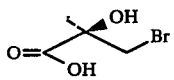

(d) reducing said bromo-acid with a mixture of borane-tetrahydrofuran forming a bromodiol of the formula:

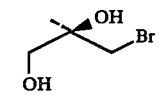

(e) treating said bromodiol with dimethoxypropane and toluenesulfonic acid forming an acetonide of the formula:

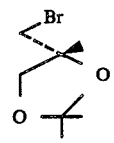

(f) reacting said acetonide with dipropyl cuprate forming an alkylation product of the formula:

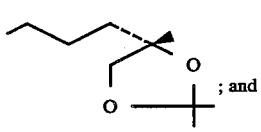

(g) reacting said alkylation product with acidic, aqueous tetrahydrofuran to effect formation of (−)S-2-methyl-hexane-1,2-diol.

5. The method of claim 4 wherein the base according to step (a) thereof is sodium hydroxide.

6. The method of claim 4 wherein the aprotic polar solvent according to step (b) thereof is dimethylformamide.

* * * * *